United States Patent
Abovitz et al.

(10) Patent No.: US 10,722,318 B2
(45) Date of Patent: Jul. 28, 2020

(54) SURGICAL TOOLS FOR SELECTIVELY ILLUMINATING A SURGICAL VOLUME

(75) Inventors: Rony Abovitz, Hollywood, FL (US); Hyosig Kang, Weston, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 782 days.

(21) Appl. No.: 13/216,926

(22) Filed: Aug. 24, 2011

(65) Prior Publication Data

US 2013/0053648 A1 Feb. 28, 2013

(51) Int. Cl.

| | | |
|---|---|---|
| *A61B 90/30* | (2016.01) | |
| *A61B 90/92* | (2016.01) | |
| *A61B 34/00* | (2016.01) | |
| *A61B 1/06* | (2006.01) | |
| *A61B 34/20* | (2016.01) | |
| *A61B 90/00* | (2016.01) | |

(52) U.S. Cl.
CPC ............. *A61B 90/30* (2016.02); *A61B 34/76* (2016.02); *A61B 90/92* (2016.02); *A61B 1/06* (2013.01); *A61B 1/0684* (2013.01); *A61B 34/20* (2016.02); *A61B 2034/2055* (2016.02); *A61B 2090/0807* (2016.02); *A61B 2090/309* (2016.02)

(58) Field of Classification Search
CPC .......... A61B 17/00; A61B 17/22; A61B 1/32; A61B 5/05; A61B 6/00; A61B 90/36; A61B 1/06; A61B 1/0684; A61B 2034/2055; A61B 2090/0807; A61B 2090/309; A61B 34/20; A61B 34/76; A61B 90/30; A61B 90/92; G09G 5/02; G06G 7/58; H04N 7/18

USPC .... 606/1, 130; 600/245, 407, 427, 476, 424; 345/629; 348/77; 703/11; 362/119
See application file for complete search history.

(56) References Cited

U.S. PATENT DOCUMENTS

| | | | | |
|---|---|---|---|---|
| 4,651,732 A | * | 3/1987 | Frederick | 606/130 |
| 4,870,952 A | * | 10/1989 | Martinez | A61B 1/00117 362/572 |
| 6,002,859 A | * | 12/1999 | DiGioia et al. | 703/11 |
| 6,129,662 A | * | 10/2000 | Li | G02B 6/0006 362/572 |
| 6,166,744 A | * | 12/2000 | Jaszlics et al. | 345/629 |
| 6,176,824 B1 | * | 1/2001 | Davis | A61B 1/24 600/178 |
| 6,205,411 B1 | * | 3/2001 | DiGioia, III | A61B 17/15 623/901 |
| 6,675,040 B1 | * | 1/2004 | Cosman | 600/427 |

(Continued)

OTHER PUBLICATIONS

Eric Acosta and Alan Liu 'Real-time volumetric haptic and visual burrhole simulatio' National Capital Area Medical Simulation Center Uniformed Services University Article Dated 2007.

*Primary Examiner* — Gary Jackson
*Assistant Examiner* — Jonathan T Kuo
(74) *Attorney, Agent, or Firm* — Foley & Lardner LLP (57) ABSTRACT

A device for providing a colorfield for guiding a surgical tool within a surgical volume is provided. The device may include a coupling mechanism configured to couple the device to a surgical tool, and a light source configured to selectively emit light having a first predetermined color upon at least one of a surgical volume and the surgical tool. The first predetermined color may be selected based, at least in part, on a current spatial position of a portion of the surgical tool relative to a first pre-defined zone within the surgical volume.

21 Claims, 4 Drawing Sheets

(56) References Cited

U.S. PATENT DOCUMENTS

| | | | |
|---|---|---|---|
| 6,827,723 B2* | 12/2004 | Carson | 606/130 |
| 7,020,370 B2* | 3/2006 | Harris | G02B 6/0005 |
| | | | 359/291 |
| 7,072,707 B2* | 7/2006 | Galloway, Jr. | A61B 90/36 |
| | | | 600/407 |
| 7,114,500 B2* | 10/2006 | Bonutti | A41D 19/0157 |
| | | | 128/851 |
| 7,206,626 B2* | 4/2007 | Quaid, III | 600/407 |
| 7,270,439 B2* | 9/2007 | Horrell | A61B 90/36 |
| | | | 362/119 |
| 7,306,559 B2* | 12/2007 | Williams | A61B 17/02 |
| | | | 600/245 |
| 7,383,073 B1* | 6/2008 | Abovitz et al. | 600/407 |
| 7,392,076 B2* | 6/2008 | Moctezuma de La Barrera | |
| | | | 600/427 |
| 7,728,868 B2* | 6/2010 | Razzaque et al. | 348/77 |
| 7,751,870 B2* | 7/2010 | Whitman | 600/476 |
| 7,874,982 B2* | 1/2011 | Selover | A61B 17/02 |
| | | | 600/199 |
| 8,430,813 B2* | 4/2013 | Selover et al. | 600/245 |
| 8,506,565 B2* | 8/2013 | DeCarlo | A61B 18/1402 |
| | | | 606/42 |
| 8,617,077 B2* | 12/2013 | van Groningen | A61B 8/546 |
| | | | 600/439 |
| 2003/0060831 A1* | 3/2003 | Bonutti | A61B 17/1675 |
| | | | 606/86 R |
| 2004/0106916 A1* | 6/2004 | Quaid et al. | 606/1 |
| 2005/0128184 A1* | 6/2005 | McGreevy | A61B 18/1206 |
| | | | 345/156 |
| 2006/0069313 A1* | 3/2006 | Couvillon, Jr. | A61B 5/064 |
| | | | 600/179 |
| 2006/0142657 A1* | 6/2006 | Quaid | A61B 17/1764 |
| | | | 600/424 |
| 2007/0102005 A1* | 5/2007 | Bonutti | A61F 2/3859 |
| | | | 128/849 |
| 2007/0142751 A1 | 6/2007 | Kang et al. | |
| 2008/0047567 A1* | 2/2008 | Bonutti | A61B 46/00 |
| | | | 128/852 |
| 2009/0012532 A1 | 1/2009 | Quaid et al. | |
| 2009/0054890 A1* | 2/2009 | DeCarlo | A61B 18/1402 |
| | | | 606/34 |
| 2011/0230794 A1* | 9/2011 | van Groningen | A61B 8/546 |
| | | | 601/2 |

* cited by examiner

SURGICAL TOOLS FOR SELECTIVELY ILLUMINATING A SURGICAL VOLUME

TECHNICAL FIELD

The present disclosure relates generally to surgical tools, and more particularly, to devices and methods for displaying a colorfield and guiding a surgical tool within a surgical volume.

BACKGROUND

Surgical tools are commonly known in the art as valuable aids for surgeons performing surgical procedures. Such surgical tools may be especially helpful in minimally invasive surgery (MIS), or surgical procedures that are performed through incisions that are considerably smaller than incisions used in traditional surgical approaches. In an orthopedic application such as total knee replacement surgery, for example, an MIS incision length may be in a range of about 4 to 6 inches whereas an incision length in traditional total knee surgery is typically in a range of about 6 to 12 inches. Although MIS procedures are more difficult to perform due to the limitations associated with smaller incisions, there are several advantages to the less invasive MIS procedures which promote continued use thereof. For instance, the smaller incisions of MIS procedures may help minimize trauma to soft tissue, reduce post-operative pain, promote earlier mobilization, shorten hospital stays and speed rehabilitation of the patient. Accordingly, it is a shared goal in the art to overcome the common drawbacks associated with MIS procedures and minimize the difficulties surgeons face while performing MIS procedures.

One drawback of MIS is that the small incision size reduces a surgeon's ability to view and access the anatomy of a region of interest or surgical volume. For example, in minimally invasive orthopedic joint replacement, limited visibility and limited access to the joint increase the complexity of assessing proper implant position and of reshaping bone. As a result, accurate placement of implants may be more difficult. Conventional techniques for counteracting these problems include, for example, surgical navigation, positioning the leg for optimal joint exposure, and employing specially designed, downsized instrumentation and complex surgical techniques. Such techniques, however, typically require a large amount of specialized instrumentation, a lengthy training process, and a high degree of skill. Moreover, the operative results among various surgeons may not be sufficiently predictable, repeatable and/or accurate. In other related applications, due to the limited visibility of MIS procedures, the surgeon may refer to a display screen through which the surgeon may view a two- or three-dimensional model of the region of interest derived from compilations of medical images.

A common drawback of both MIS and traditional surgical approaches in orthopedic applications is that healthy as well as diseased bone is removed during preparations for an implant. For example, a total knee replacement can require removal of up to ½ inch of bone on each of three compartments of the knee. One conventional solution for preserving healthy bone is to perform a partial, unicompartmental or multicompartmental, knee replacement, which involves removal of damaged or arthritic portions on only one compartment of the knee. Such an approach may rely on freehand sculpting of bone with a spherical burr through a minimally invasive incision typically about 3 inches in length. While the spherical burr enables cuts having rounded shapes which cannot be reproduced with a surgical saw, the freehand burring technique is difficult to master and requires more artistic sculpting capability from the surgeon than techniques employing traditional cutting jigs or saw guides. Accordingly, while freehand cutting requires a high degree of skill to achieve operable results that are sufficiently predictable, repeatable and/or accurate, unicompartmental and traditional surgery typically result in the removal of at least some healthy bone along with the diseased and/or damaged bone.

One approach to orthopedic surgeries makes use of autonomous robotic systems to aid the surgeon. A drawback of the use of autonomous robotic systems is that such approaches do not enhance the surgeon's inherent surgical skill in a cooperative manner. Such systems, however, primarily serve to enhance bone machining by performing autonomous cutting with a high speed burr or by moving a drill guide into place and holding the position of the drill guide while the surgeon inserts cutting tools through the guide. These systems act autonomously rather than cooperatively with the surgeon, and thus, require the surgeon to cede a degree of control to the robot. Additional drawbacks of autonomous systems may include poor ergonomics, the need to rigidly clamp the bone during registration and cutting, increased incision length for adequate robot access, and limited acceptance by surgeons and regulatory agencies due to the autonomous nature of the system.

Accordingly, there is a need for a more simplified surgical device, system or method that provides for more predictable, repeatable and accurate surgical procedures. More specifically, there is a need to minimize the amount of healthy bone that is removed with damaged and/or diseased bone, minimize autonomous control and increase the overall control of the surgeon performing surgical procedures. Furthermore, there is a need to enable the surgeon to maintain direct visual contact with the anatomy and to reduce any latency associated with surgical or guide tools.

SUMMARY OF THE DISCLOSURE

In one aspect of the present disclosure, a medical device is provided. The device may include a light source associated with a surgical tool that is configured to selectively emit light having a first predetermined color upon at least one of a surgical volume and the surgical tool. The first predetermined color may be selected based, at least in part, on a current spatial position of the surgical tool relative to a first pre-defined zone within the surgical volume.

In another aspect of the disclosure, a surgical system is provided. The surgical system may include a surgical tool, an illumination device coupled to the surgical tool, and a computer system in communication with the illumination device. The illumination device may include a light source configured to selectively emit light having a first predetermined color upon at least one of a surgical volume and the surgical tool. The computer system may be configured to track a current spatial position of the surgical tool relative to a first pre-defined zone within the surgical volume, and select the first predetermined color for illumination based, at least in part, on the current spatial position of the surgical tool.

In yet another aspect of the disclosure, a method for providing a colorfield for guiding a surgical tool within a surgical volume is provided. The method may track a current spatial position of the surgical tool relative to the surgical volume, emit light having a first predetermined color upon at least one of the surgical volume and the surgical tool if the current spatial position of the surgical tool corresponds to a first pre-defined zone of the surgical volume, and emit light having a second predetermined color upon at least one of the surgical volume and the surgical tool if the current spatial position of the surgical tool corresponds to a second pre-defined zone of the surgical volume. The second predetermined color being different from the first predetermined color.

DETAILED DESCRIPTION

Reference will now be made in detail to specific embodiments or features, examples of which are illustrated in the accompanying drawings. Generally, corresponding reference numbers will be used throughout the drawings to refer to the same or corresponding parts. Although the following disclosure may make certain references to orthopedic procedures involving knee joints, it should be understood that the subject matter described herein is applicable to other joints in the body, such as, for example, shoulders, elbows, wrists, spines, hips, ankles, and the like.

Figure 1:
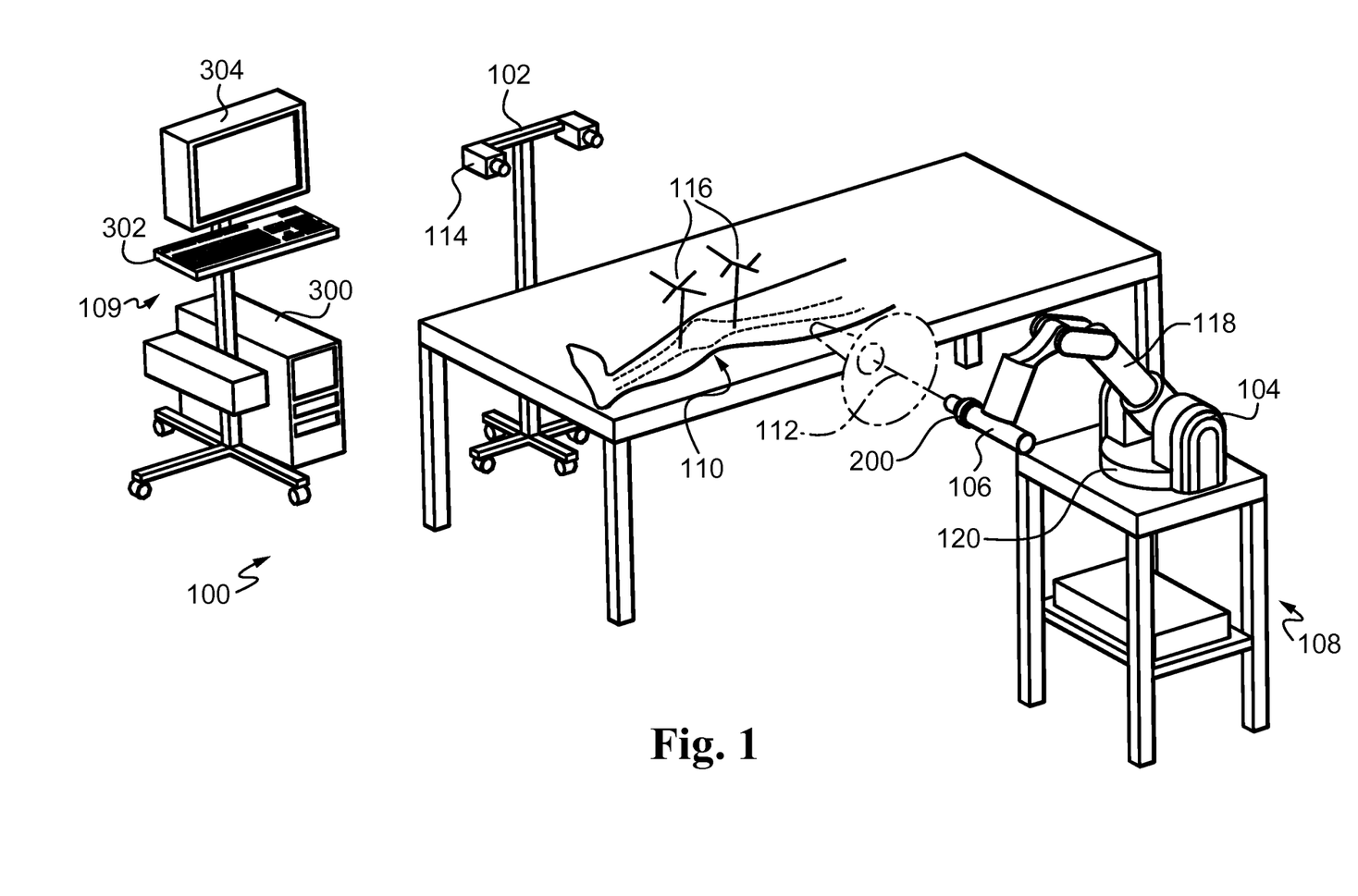
FIG. 1 is a graphical view of an exemplary surgical system.

Referring to FIG. 1, one exemplary environment within which a surgical system 100 may be used is provided. As shown, the surgical system 100 may generally provide a tracking device 102, a haptic device 104, a surgical tool 106 in electrical communication with the haptic device 104, and one or more computer systems 108, 109. The surgical system 100 may be used as an aid in planning and/or performing surgical work upon an anatomical region or surgical volume 110, for example, the knee joint of FIG. 1. More specifically, the tracking device 102 and the haptic device 104 may be used to assist the user in guiding the surgical tool 106 within the surgical volume 110, while the computer systems 108, 109 may be used to manage the overall operation of the surgical system 100. Actual work on the surgical volume 110 may be performed by controlling the surgical tool 106 and manipulating a working end 112 of the surgical tool 106 to perform surgery, surgical planning and/or surgical navigation, as described, for example, in U.S. patent application Ser. No. 11/357,197 (Pub. No. 2006/0142657), filed Feb. 21, 2006, which is hereby incorporated by reference.

The tracking device 102 may include means for tracking movement within the anatomical region of interest or surgical volume 110. In particular, the tracking device 102 may include a detector 114 and one or more spatially detectable markers 116 that are disposed near the surgical volume 110. The markers 116 may be positioned at relevant sections of the anatomy, for example, on the tibia and the femur connected to and forming, at least in part, the knee joint in FIG. 1. By tracking markers 116 that are affixed about the surgical volume 110, the detector 114 may be able to track movement within the surgical volume 110 and enable compensation for any such movement in real-time. The tracking device 102 may additionally include apparatus for tracking the spatial position and orientation of the surgical tool 106 relative to the markers 116, and thus, the surgical volume 110. For example, the tracking device 102 may be configured to track a unique identifier on or within the surgical tool 106 and/or the working end 112 thereof. Alternatively, information provided by the tracking device 102 may be used in conjunction with the net displacement of the surgical tool 106 as detected by the haptic device 104 in order to determine the spatial location of the surgical tool 106 relative to the surgical volume 110. Based on such tracking techniques and using known geometric relationships between the surgical volume 110 and the markers 116, the surgical system 100 may be able to track the spatial position and orientation, as well as the velocity and/or acceleration, of the surgical tool 106 relative to the markers 116 and the surgical volume 110.

The haptic device 104 and the surgical tool 106 coupled thereto may be manipulated by the user while performing surgical procedures upon the surgical volume 110. As shown in FIG. 1, for example, the haptic device 104 may include a haptic arm 118 that is movable relative to its base 120 and adapted to transmit haptic feedback, or tactile stimulations such as vibrations, pulses, force and/or torque feedback, to the user. Additionally, the joints and/or hinges of haptic device 104 may be fitted with position sensors, encoders, or the like, configured to communicate data pertaining to the spatial position, orientation, velocity and/or acceleration of the surgical tool 106 relative to at least the base 120 thereof. The haptic device 104 may further aid user manipulation of the surgical tool 106 by selectively providing haptic feedback corresponding to one or more pre-defined zones within the surgical volume 110, that the surgical tool 106 is approaching. The pre-defined zones within the knee joint of FIG. 1, for example, may be determined according to a pre-operative or intra-operative plan and may define working zones relating to portions of the knee joint intended for resection, restricted zones relating to portions of the knee joint that are not intended for resection, and intermediate zones relating to portions of the knee joint that are proximate to a boundary between a working zone and a restricted zone. Depending on the desired application, each zone may be defined to be exclusive to one another, or alternatively, one or more of the zones may be defined to be at least partially inclusive of another zone. For example, in one embodiment, the intermediate zone may be defined by a boundary at least partially including a section of the working and/or restricted zones. In yet another embodiment, the intermediate zone may be defined by a boundary that is situated between the boundaries of the working and restricted zones and exclusive of each of the working and restricted zones. A spatial mapping of the pre-defined zones within the surgical volume 110 as well as their respective boundaries may be observed using the computer systems 108, 109 and derived based on a compilation of medical images and input from the surgeon during the pre-operative and/or intra-operative planning. The medical images may be provided by medical imaging devices commonly used in the art, such as computed tomography (CT) devices, magnetic resonance imaging (MRI) devices, fluoroscopic devices, ultrasound devices, and the like. Based on the mapped locations of the pre-defined zones within the surgical volume 110, the computer systems 108, 109 may communicate the boundaries of the zones to the haptic device 104 in terms of control parameters or limits within which the haptic arm 118 and the surgical tool 106 are permitted to move. For example, the haptic device 104 may limit the user's ability to physically move a surgical tool 106 beyond the boundaries of a working zone by electromechanically resisting manipulation of the haptic arm 118 and the associated surgical tool 106 in a particular direction. The haptic device 104 may additionally provide feedback in the form of tactile vibrations, pulses, force feedback, torque feedback, and the like, configured to sufficiently enable the user to distinguish between the different zones within the surgical volume 110.

Figure 2:
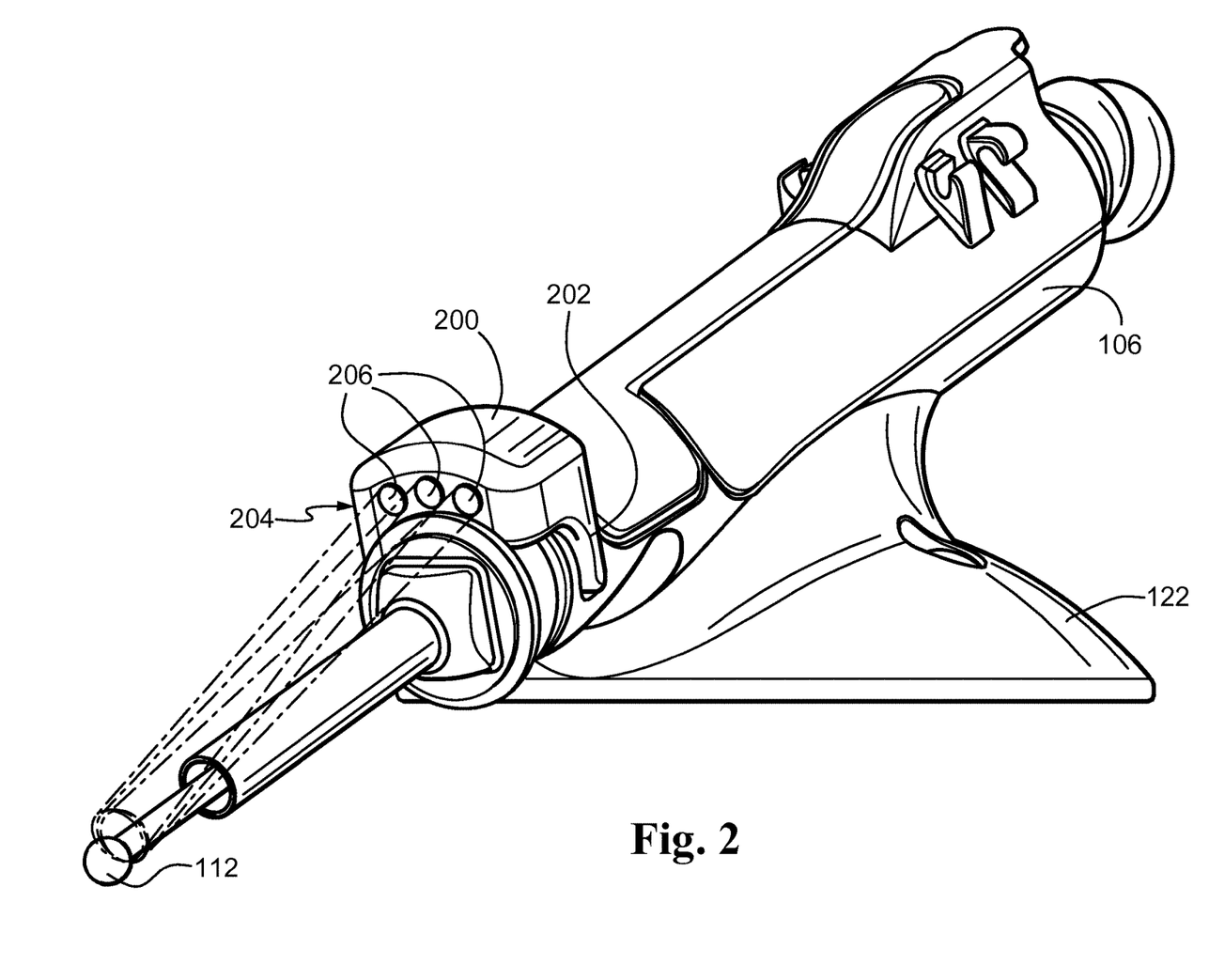
FIG. 2 is a graphical view of an exemplary embodiment of an illumination device as provided on a surgical tool.

Turning to FIG. 2, one exemplary embodiment of an illumination device 200 that may be used in conjunction with the surgical tool 106 is provided. As shown, the surgical tool 106 may include a tool base 122 which may be coupled to, for example, a distal end of the arm 118 of the haptic device 104 of FIG. 1. The working end 112 of the surgical tool 106 may include, for example, a burr, a drill, a probe, a saw, a microscope, a laser range finder, a camera, an endoscope, an ultrasound probe, an irrigation device, a suction device, a radiotherapy device, or any other suitable medical device. The illumination device 200 may include a coupling mechanism 202 and a light source 204. The coupling mechanism 202 may be sized and configured such that the illumination device 200 may be removably coupled to the surgical tool 106. For example, the coupling mechanism 202 may take the form of a clip, ring, screw, or any other suitable fastener for removably coupling the illumination device 200 to the body of the surgical tool 108. The light source 204 of the illumination device 200 may include a plurality of lighting devices 206, such as light emitting diodes (LEDs), organic light emitting diodes (OLEDs), or any other converging array of lighting devices capable of emitting visible light in different colors. Alternatively, the light source 204 may be a projection device such as a picoprojector or the like. Alternatively still, the light source 204 may include a single lighting device 206 that is capable of emitting a plurality of different colors, or any other device known in the art for selectively emitting light having a predetermined color. While the haptic device 104 may employ haptic feedback to guide user manipulation of the surgical tool 106, the illumination device 200 may similarly employ colored lights or a colorfield to signal to the user whether it is safe to proceed with the surgical tool 106 in an intended direction. Accordingly, the light source 204 may be configured to provide a colorfield on or near the surgical tool 106 for example, the working end 112 of the surgical tool 106, or within the surgical volume 110, such that any one or more of the colors emitted are readily visible to the user while viewing the surgical volume 110. Furthermore, the light source 204 may be configured such that the colorfield corresponds to the spatial position, orientation, velocity and/or acceleration of the surgical tool 106 relative to the surgical volume 112 and the pre-defined zones therein. In one particular embodiment, the light source 204 may be configured to illuminate only one of a green, white or red colorfield based on the immediate spatial position and orientation of the surgical tool 106. For example, if the spatial position and orientation of the surgical tool 106 corresponds to a working zone within which surgical work is anticipated according to a pre-operative or intra-operative plan, the light source 204 may provide a green colorfield to signal to the user that it is safe to continue work in the immediate zone. If the spatial position and orientation of the surgical tool 106 corresponds to a restricted zone within which surgical work is not anticipated according to a pre-operative or intra-operative plan, the light source 204 may provide a red colorfield to signal to the user to stop and revise the path of manipulation accordingly. Additionally, if the spatial position and orientation of the surgical tool 106 indicates that the surgical tool 106 is in an intermediate zone proximate to a boundary between the working zone and the restricted zone, the light source 204 may provide a white colorfield to signal to the user to signal such proximity to the boundary. In alternative modifications, the illumination device 200 and the light source 204 may be configured to associate different combinations of colorfields with different types of zoning constraints. In yet another embodiment, the illumination device 200 and the light source 204 may be configured to project shapes and/or symbols into the surgical volume 110. In still another embodiment, the illumination device 200 and the light source 204 may be configured to project text, numbers, and/or other data into the surgical volume 110.

According to one embodiment in which the illumination device 200 is not used with a haptic device 104 preventing movement of the surgical tool 106 into a restricted zone, the surgical system 100 may be configured to depower the surgical tool 106 if the user moves the surgical tool into a restricted zone despite the red colorfield. In this instance, the computer systems, 108, 109 may cause the light source 204 to provide a predetermined colorfield to signal to the user that the surgical system 100 intentionally depowered the surgical tool 106, as opposed to a failure of power system. Similarly, light source 204 may utilized to provide predetermined colorfield to signals to indicate to the user that the haptic device 104 is in a particular mode, such as free mode, approach mode, or haptic mode. In free mode, the user has full control of the haptic device 104 in any direction, but the surgical tool 106 is depowered. In approach mode, the user may have partial or full haptic guidance to a target location, but the surgical tool 106 is depowered. In haptic mode, the user can power the surgical tool 106 and perform work in the working zone with haptic guidance.

Figure 3:
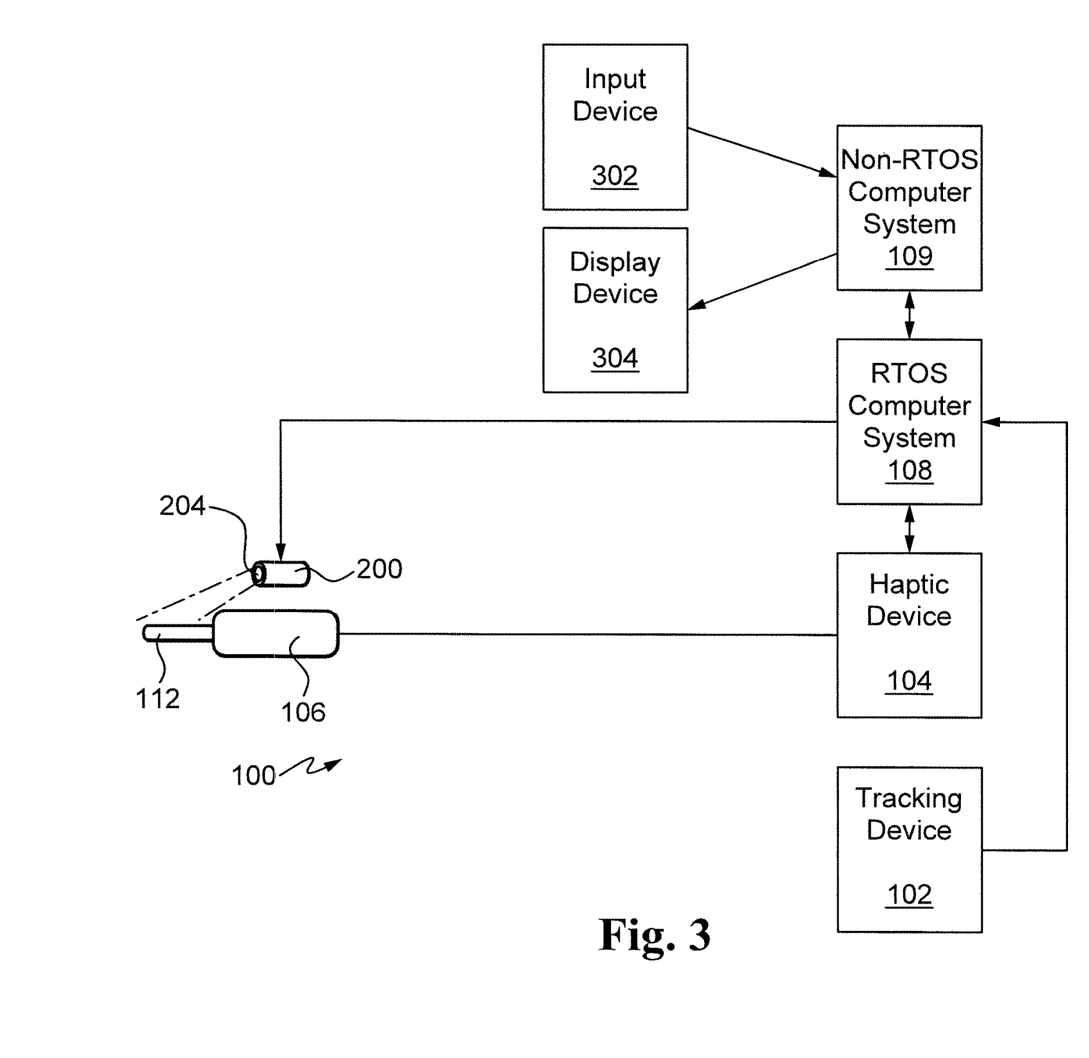
FIG. 3 is a diagrammatic view of an exemplary illumination device as applied to a surgical system.

The control signals or parameters that are communicated to the illumination device 200 may relate to information regarding the spatial locations and boundaries of the pre-defined zones within the surgical volume 110 as well as the spatial position, orientation, velocity and/or acceleration of the surgical tool 106. In order for the light source 204 to illuminate with the appropriate color throughout a surgical procedure, the illumination device 200 may be updated with the appropriate control parameters at a consistently fast rate, or for example, in real-time. As shown in FIG. 3, the illumination device 200 may be configured to be in communication with the computer system 108, which may include a real-time operating system, as discussed below. The computer system 108 may be in further communication with the haptic device 104, the tracking device 102, and the computer system 109, which may include a non-real-time operating system. The computer system 109 may be in further communication with the input device 302 and the display device 304, and the haptic device 104 may be in further communication with the surgical tool 106. Accordingly, the computer system 108 may communicate the appropriate signals to the light source 204, and further, enable the light source 204 to dynamically emit colorfields corresponding to the current spatial position, orientation, velocity and/or acceleration of the surgical tool 106. Moreover, signal communications between each of the tracking device 102, haptic device 104, surgical tool 106, computer systems 108, 109 and the illumination device 200 of FIG. 3 may be wired, wireless, or a combination thereof.

The computer systems 108, 109 of FIG. 1 may generally include hardware and software configured to efficiently manage the overall operation of the surgical system 100. As shown, the computer systems 108, 109 may provide a computer 300 that is in communication with at least an input device 302 and a display device 304. The computer 300 may be in wired or wireless communication with one or more of the tracking device 102, the haptic device 104, the surgical tool 106 and the illumination device 200. The input device 302 may include a keyboard, a mouse, a trackball, a touch screen, a touch pad, a microphone, a dial, a switch, a button, a camera, or any other device suitable for inputting information directly into the computer 300. The display device 304 may include a liquid crystal display (LCD), a cathode ray tube (CRT) display, a plasma screen, a touch screen, and/or any other output device for visually interfacing with the computer 300. The computer 300 of FIG. 1 may further be in communication with, or have stored therein, medical images of the anatomy of the surgical volume 110, as obtained by CT devices, MRI devices, fluoroscopic devices, ultrasound devices, and the like. Based on the medical images, the computer 300 may generate two- or three-dimensional models of the surgical volume 110 which may further be graphically manipulated by the user via the input device 302 and viewed via the display device 304. Among other things, the models may include spatial mapping information pertaining to the pre-defined zones within the surgical volume 110. The computer 300 may further integrate the mapped zones with tracking information provided by the tracking device 102 and/or the haptic device 104 so as to generate and communicate the appropriate signals or control parameters to the haptic device 104 and/or the illumination device 200. More specifically, to the haptic device 104, the control parameters may communicate the different degrees and/or types of haptic feedback to be used for the different pre-defined zones within the surgical volume 110, while, to the illumination device 200, the control parameters may communicate the different colorfields to be used for the different pre-defined zones.

With further reference to FIG. 1, the computer systems 108, 109 may comprise one or more architectures that are independently configurable so as to enable more effective tracking of the surgical tool 106 within the surgical volume 110. For example, the first computer system 108 may include a real-time operating system (RTOS) configured to provide stable and higher-priority updates to the surgical tool 106 and the illumination device 200 during a surgical procedure. More specifically, the first computer system 108 may be preprogrammed with algorithms which operate based on a clock dedicated solely to the function of reading and responding to data provided by the tracking device 102. As a result, the first computer system 108 may be able to continuously monitor for any changes in the surgeon's placement of the surgical tool 106 relative to the pre-defined zones within the surgical volume 112 and, if necessary, immediately change the color emitted by the illumination device 200 and/or alter the haptic feedback provided by the haptic device 104 with minimal delay. The second computer system 109 of FIG. 1 may operate independently of the first computer system 108 and provide a non-RTOS that may be used with more tolerant or lower-priority functions for which real-time updates are not as critical. For instance, the second computer system 109 may be configured with algorithms which also monitor for changes in the surgeon's placement of the surgical tool 106 within the surgical volume 112 but at less stringent sampling intervals as compared with the RTOS of the first computer system 108. The second computer system 109 may be configured to receive discrete data from the tracking device 102 sampled at frequencies, for example, approximately ranging from 30 Hz to 500 Hz. To compensate for the discrete data, the second computer system 109 may employ filters to digitally condition the tracking data. For example, the non-RTOS may apply noise filters and/or interpolation filters to smooth and populate gaps between the data. The interpolated tracking information may then be applied to coordinate transform processes which map or align spatial coordinates of the surgical volume 112 onto, for example, a three-dimensional model to be graphically displayed to the surgeon for guidance. The coordinate transform process may include any suitable transformation technique, such as, for example, rigid-body transformation, non-rigid transformation, affine transformation, and the like. Accordingly, during surgical procedures, the surgeon may rely on real-time color-coded guidance provided directly at the surgical tool 106 by the illumination device 200 and the first computer system 108, while also periodically referring to a graphical display of the surgical volume 112 provided by the display device 304 and the second computer system 109.

Figure 4:
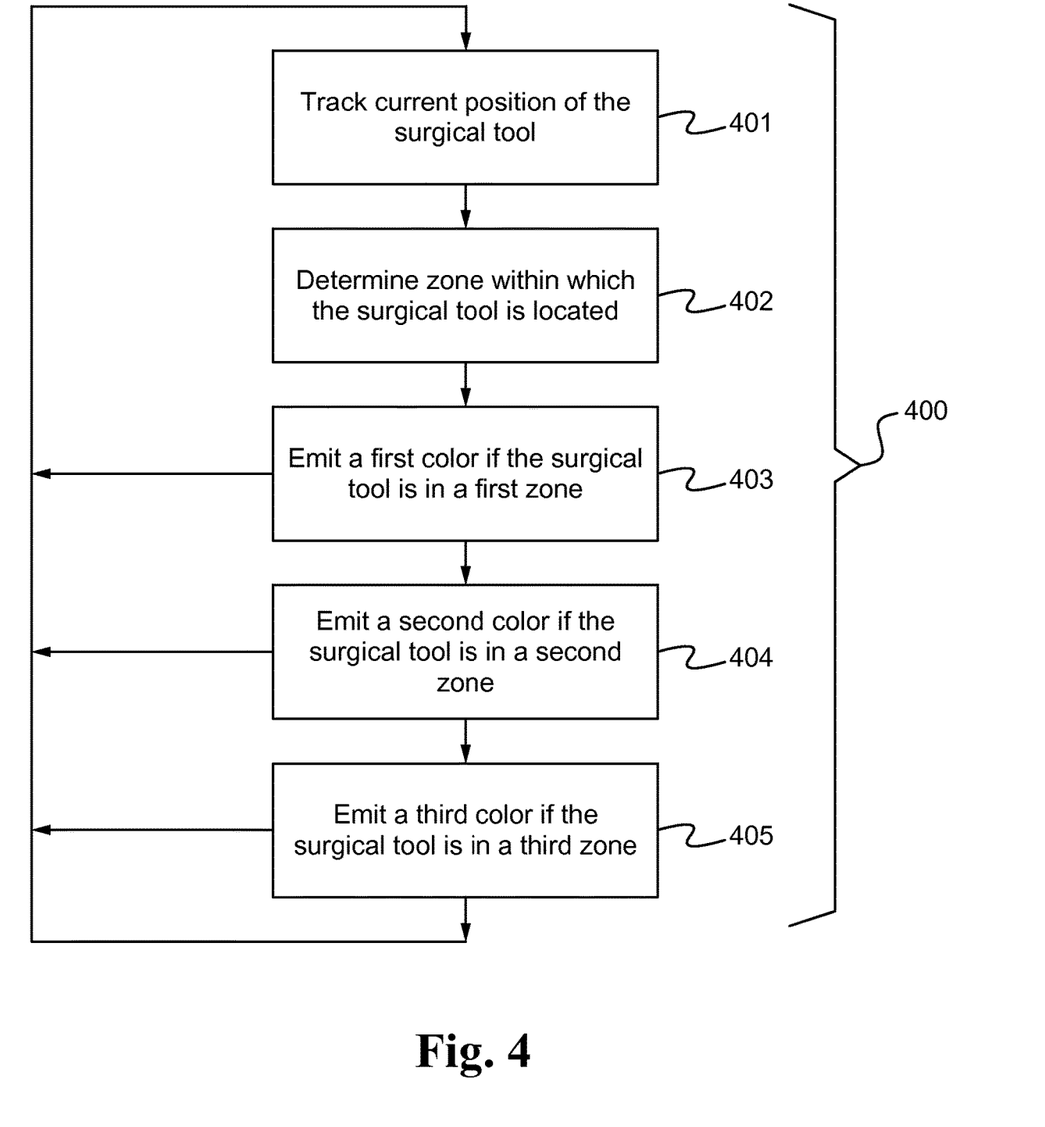
FIG. 4 is a flow diagram of one exemplary method of providing a colorfield using an illumination device.

Turning to the embodiment of FIG. 4, an exemplary algorithm or method 400 by which the computer 300 of the computing device 108 may enable a colorfield upon a surgical tool 106 is provided. Specifically, the hardware of the computer 300 may include any suitable combination of controllers, processors, memory, and the like, that may be preprogrammed with software for configuring the computer 302 to function according to, for example, steps 401-404 of FIG. 4. As shown in step 401, the computer 300 may initially be configured to track at least the current spatial position and orientation of the surgical tool 106 relative to the surgical volume 110. For example, the computer 300 may be configured to continuously receive and monitor the tracking information provided by one or more of the tracking device 102 and the haptic device 104. In alternative embodiments, the computer 300 may additionally be configured to track the current velocity and/or acceleration of the surgical tool 106. In step 402, the computer 300 may be configured to determine the current pre-defined zone of the surgical volume 110 within which the surgical tool 106 is located. For example, based on pre-defined models which map the spatial locations of the pre-defined zones within the surgical volume 110, and further, based on the tracking information obtained in step 401, the computer 300 may determine the specific zone which corresponds to the current location of the surgical tool 106. Furthermore, in steps 403-405, the computer 300 may be configured to enable a colorfield corresponding to the current zone determined in step 402. In step 403, for example, if the current zone is determined to be a first zone, such as a working zone within which surgical work is anticipated according to a pre-operative or intra-operative plan, the computer 300 may instruct the illumination device 200 to illuminate a colorfield of a first color, such as green, to signal to the user that it is safe to continue work in that zone. Similarly, in step 404, for example, if the current zone is determined to be a second zone, such as a restricted zone within which surgical work is not anticipated according to a pre-operative or intra-operative plan, the computer 300 may instruct the illumination device 200 to illuminate a colorfield of a second color, such as red, to signal to the user to stop and revise the path of manipulation accordingly. Additionally, in an optional step 405, for example, if the immediate zone is determined to be an intermediate zone, such as a zone proximate to a boundary between the working zone and the restricted zone, the computer 300 may instruct the illumination device 200 to illuminate a colorfield of a third color, such as white, to signal to the user such proximity to the boundary. Once the appropriate colorfield is illuminated, the computer 300 may return to steps 401-402 to detect for any further changes to the location of the surgical tool 106 and to change the colorfield accordingly. The computer 300 may also be configured to execute steps 401-402 with any of steps 403-405 of FIG. 4 concurrently so as to provide real-time colorfield response to changes in the spatial position and orientation of the surgical tool 106. Based on the foregoing, it can be seen that the present disclosure provides a simplified device, system and method that provides enhanced information to a surgeon during surgical procedures.

While only certain embodiments have been set forth for the purposes of illustration, alternatives and modifications will be apparent from the above description to those skilled in the art. These and other alternatives are considered equivalents and within the spirit and scope of this disclosure and the appended claims.

What is claimed is:

1. A medical device, comprising:
   a light source associated with a surgical tool, wherein the surgical tool is configured to perform surgical work within a surgical volume and the light source is configured to project one or more characters onto a portion of the surgical volume; and
   a controller configured to control the light source based on at least one of a location, an orientation, a velocity, or an acceleration of the surgical tool.

2. The medical device of claim 1, wherein the controller is configured to control the light source to provide a first predetermined color when the surgical tool is within a first pre-defined zone of the surgical volume and a second predetermined color when the surgical tool is within a second pre-defined zone of the surgical volume.

3. The medical device of claim 2, wherein the first pre-defined zone is a working zone and the second pre-defined zone is a restricted zone.

4. The medical device of claim 2, wherein the controller is configured to control the light source to provide a third predetermined color when the surgical tool is within an intermediate zone, the third predetermined color being different from both the first predetermined color and the second predetermined color.

5. The medical device of claim 2, wherein the first pre-defined zone is a working zone, and wherein the second pre-defined zone is a restricted zone.

6. The medical device of claim 5, wherein the first predetermined color is green, and wherein the second predetermined color is red.

7. The medical device of claim 1, wherein the light source is configured to be fixedly disposed relative to a working end of the surgical tool such that the light source is oriented to additionally illuminate the working end of the surgical tool with the colorfield.

8. The medical device of claim 1, wherein the controller is in communication with a computer system, and wherein the non-real time non-real-time computer system provides a virtual display of the surgical volume to a user.

9. The medical device of claim 8, wherein:
   the virtual display of the surgical volume displays a representation of a pre-defined zone;
   the controller is configured to control the light source to project light of a first predetermined color when the surgical tool is oriented toward the first pre-defined zone; and
   wherein the first pre-defined zone is at least one of a working zone, a restricted zone and an intermediate zone.

10. The medical device of claim 1, wherein the one or more characters comprise one or more letters.

11. The medical device of claim 1, wherein the controller is configured to control the light source to vary the color of the colorfield based on a pre-operative surgical plan.

12. The medical device of claim 1, wherein the one or more characters comprise one or more numbers.

13. The medical device of claim 1, wherein the one or more characters comprises one or more shapes.

14. The medical device of claim 1, wherein the one or more characters are configured to represent data.

15. A surgical system, comprising:
   a surgical tool;
   an illumination device coupled to the surgical tool, the illumination device having a light source configured to selectively project one or more characters onto a surgical field;
   a computer system in communication with the illumination device, the computer system being configured to control the light source based on at least one of a location, an orientation, a velocity, or an acceleration of the surgical tool.

16. The surgical system of claim 15, wherein the computer system is configured to control the light source to emit visible light having a first predetermined color when a working end of the surgical tool is within a working zone and having a second predetermined color when the working end of the surgical tool is within a restricted zone, the second predetermined color being different from the first predetermined color.

17. The surgical system of claim 16, wherein computer system is configured to control the light source to emit visible light having a third predetermined color when the working end of the surgical tool is within an intermediate zone, the third predetermined color being different from both the first predetermined color and the second predetermined color.

18. The surgical system of claim 16, wherein the computer system includes a real-time operating system configured to select between the first predetermined color and the second predetermined color.

19. The surgical system of claim 18, wherein the real-time operating system is configured to provide a signal to the light source prompting the light source to emit visible light having one of the first predetermined color and the second predetermined color.

20. The surgical system of claim 19, wherein the computer system includes a non-real-time operating system configured to provide a virtual display of the surgical volume to a user.

21. The surgical system of claim 20, wherein the virtual display of the surgical volume displays a representation of the working zone and the restricted zone, and wherein the virtual display represents the working zone with the first predetermined color, and the restricted zone with the second predetermined color.

* * * * *